(12) United States Patent
Resconi et al.

(10) Patent No.: US 7,115,761 B2
(45) Date of Patent: Oct. 3, 2006

(54) PROCESS FOR THE PRODUCTION OF MONOHALIDE OR DIHALIDE METALLOCENE COMPOUNDS

(75) Inventors: Luigi Resconi, Ferrara (IT); Davide Balboni, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 11/237,588

(22) Filed: Sep. 27, 2005

(65) Prior Publication Data

US 2006/0025621 A1  Feb. 2, 2006

Related U.S. Application Data

(63) Continuation of application No. 10/474,596, filed as application No. PCT/EP02/03697 on Apr. 3, 2002, now Pat. No. 6,987,196.

(30) Foreign Application Priority Data

Apr. 10, 2001  (EP)  .................................. 01201327

(51) Int. Cl.
| C07F 17/00 | (2006.01) |
| C07F 7/00 | (2006.01) |
| C07F 9/28 | (2006.01) |
| B01J 31/00 | (2006.01) |
| C08F 4/44 | (2006.01) |

(52) U.S. Cl. ............................ 556/11; 556/12; 556/19; 556/52; 556/53

(58) Field of Classification Search ................ 556/11, 556/12, 19, 52, 53
See application file for complete search history.

(56) References Cited

U.S. PATENT DOCUMENTS

| 6,160,064 A | 12/2000 | Waymouth et al. .......... 526/160 |
| 6,175,025 B1 | 1/2001 | Kitagawa et al. ............. 556/22 |

FOREIGN PATENT DOCUMENTS

| EP | 0129368 | 12/1984 |
| EP | 0576970 | 1/1994 |
| EP | 0790076 | 8/1997 |
| EP | 0834514 | 4/1998 |
| JP | 2002088092 | 3/2002 |
| WO | 9709336 | 3/1997 |
| WO | 9936427 | 7/1999 |
| WO | 0075151 | 12/2000 |
| WO | 0153360 | 7/2001 |

OTHER PUBLICATIONS

King et al., J. Am. Chem. Soc., vol. 121, No. 2, pp. 355-366 (1999).*
Park et al. Journal of Organometallic Chemistry, vol. 535, pp. 29-32 (1997).*
Wailes et al., Journal of Organometallic Chemistry, vol. 34, pp. 155-164 (1972).*
F. R. W.P. Wild et al., "VII. Synthesis and Crystal Structure of a Chiral *ansa*-Zirconocene Derivative with Ethylene-Bridged Tetrahydroindenyl Ligands;" *Journal of Organometallic Chemistry*, 288, p. 63-67 (1985).
I. M. Lee et al., "Electronic Effects in Ziegler-Natta Polymerization of Propylene and Ethylene using Soluble Metallocene Catalysts;" *Organometallics*, 11, p. 2115-2122 (1992).
P. C. Wailes et al., "Insertion Reactions of Dicyclopentadienyldimethylzirconium and Related Cyclopentadienyl Compounds with Sulphur Dioxide and Nitric Oxide;" *Journal of Organometallic Chemistry*, 34, p. 155-164 (1972).
H. Lang et al., "Synthese und Reaktivitat von Alkinyl-substituierten Titanocen-Komplexen;" (Synthesis and Reactivity of Aklyne Substituted Titanocene Complexes); Zeitschrift fur Naturforschung, *Teil B: Anorganisch Chemie, Organische Chemie, Verlag der Zeitschrift fur Naturforschung Tubingen*, DE; vol. 45(2) 212-220 (1990).
M. Kh. Minscheva et al., "Complexes Containing Zirconium and Mercury;" *Institute of Heteroorganic Compounds*, Academy of Sciences of the USSR, Moscow. Translated from Izvestiya Akademii Nauk SSSR Seriya Khimicheskaya, No. 11, p. 2621-2623 (1976).
G. A. Razuvaev et al., "Decomposition of bis(cyclopentadienyl) derivatives of zirconium in solvents;" *Doklady Akademii Nauk SSSR*; 231(1), 114-15 (1976) (Abstract).

(Continued)

*Primary Examiner*—Porfirio Nazario-Gonzalez
(74) *Attorney, Agent, or Firm*—Jarrod N. Raphael; William R. Reid

(57) ABSTRACT

A process for preparing dihalide or monohalide metallocene compounds comprising contacting a compound of formula (II) $(Cp)(ZR^1_m)_n(A)_rML'_y$ (II) wherein Cp is a cyclopentadienyl radical; $(ZR^1_m)_n$ is a divalent bridging group between Cp and A; A is a cyclopentadienyl radical or O, S, $NR^2$, $PR^2$ wherein $R^2$ is an hydrocarbon radical, M is zirconium, titanium or hafnium. L' is an hydrocarbon radical, r ranges from 0 to 2 and y is equal to 4; with an halogenating agent selected from the group consisting of: $T^1L_{w^1}$ wherein $T^1$ is a metal of groups 3–13 of the periodic table; L is halogen and $w^1$ is equal to the oxidation state of the metal $T^1$; $T^2L_{w^2}$ wherein $T^2$ is a nonmetal element of groups 13–16 of the periodic table (new IUPAC version); and $w^2$ is equal to the oxidation state of the element $T^2$; $O=T^3L_{w^3}$ where $T^3$ is a selected from the group consisting of C, P and S; O is an oxygen atom bonded to $T^3$ through a double bond; and $w^3$ is equal to the oxidation state of the element $T^3$ minus 2; $R^6C(O)L$, wherein $R^6$ is an hydrocarbon radical; $L_2$ and HL.

5 Claims, No Drawings

OTHER PUBLICATIONS

W. A. King et al. "Absolute Metal-Ligand σBond Enthalpies in Group 4 Metallocenes. A Thermochemical, Structural, Photoelectron Spectroscopic, and ab Initio Quantum Chemical Investigation;" *J. Am. Chem. Soc.*, vol. 121(2), p. 355-366 (1999).

H. H. Brintzinger et al. "Asymmetric Thermal Transformation, a New Way to Enantiopure Biphenyl-Bridged Titanocene and Zirconocene Complexes: Efficient Catalysts for Asymmetric Imine Hydrogenation;" *J. Am. Chem. Soc.*, vol. 121(7), p. 1524-1527 (1999).

H. H. Brintzinger et al., "*ansa*-Metallocene derivatives XXXIX. Biphenyl-bridged metallocene complexes of titanium, zirconium, and vanadium: syntheses, crystal structures and enantioseparation;" *Journal of Organometallic Chemistry*, vol. 541, p. 219-232 (1997.

J. T. Park, "An efficient synthetic method of *ansa*-zirconocene dimethyl complexes via $Me_2ZrCl_2$;" *Journal of Organometallic Chemistry*, vol. 535, p. 29-32 (1997).

R. Choukroun et al., "Substituted Cyclopentadienyl Phosphinomethyl Complexes of Zirconium. Synthesis. Chemical Characteristics, Complexation with Rhodium Colmplexes, and Catalytic Properties. Molecular and Crystal Structure of $(\eta^5\text{-}t\text{-}BuC_5H_4)_2Zr(CH_2PPh_2)_2[Rh_2(\mu\text{-}S\text{-}t\text{-}Bu)_2(CO)_2]$"; *Organometallics*, vol. 9(6), p. 1982-1987 (1990).

R. D. Sanner et al., "Activation of Benzene Carbon-Hydrogen Bonds via Photolysis or Thermolysis of $(\eta^5\text{-}C_5Me_5)_2Zr(alkyl)H$. Isolation of $(\eta^5\text{-}C_5Me_5)_2Zr(C_6H_5)H$ and Its Conversion to a Complex Containing a Tetramethylfulvene Ligand;" *Organometallics*, vol. 7(4), p. 818-825 (1988).

H. Lang et al., "Zur Umsetzung von Bis(alkinyl)-Titanocenen mit Übergangsmetall-Verbindungen von Cu(II), Pd (II), Pt (II), Fe(III) und Au(III);" *Journal of Oganometallic Chemistry*, vol. 601, p. 226-232 (2000).

H. Lang et al., "Synthese und Reaktionsverhalten monomerer Bis($\eta^2$-Alkin)-Kupfer(I)-Fluorid- und-Kupfer(I)-Hydrid-Komplexe;" *Journal of Organometallic Chemistry*, vol. 553, p. 31-38 (1998).

M. Bochmann et al., "Cationic Alkylbis(cyclopentadienyl)titanium Complexes. Synthesis, Reactions with CO and *t*-BuNC, and the Structure of $[Cp_2Tl\{\eta^2\text{-}C(Me)N\text{-}t\text{-}Bu\}(CN\text{-}t\text{-}Bu)]BPh_4\bullet MeCN$;" *Organometallics*, vol. 6(12), p. 2556-2563 (1987).

M. Bochmann et al., "Synthesis and Insertion Reactions of Cationic Alkylbis(cyclopentadienyl)titanium Complexes," *J. Chem. Soc., Chem. Commun.*, p. 1610-1611 (1986).

\* cited by examiner

PROCESS FOR THE PRODUCTION OF MONOHALIDE OR DIHALIDE METALLOCENE COMPOUNDS

The present invention relates to a process for the production of monohalide or dihalide metallocene compounds in high purity and in high yields.

Metallocene compounds are well known in the art as catalyst components for the polymerization of olefins. For instance, the European Patent Application EP 0 129 368 discloses catalysts comprising mono- and di-cyclopentadienyl coordination complexes with a transition metal in combination with an alumoxane.

In those metallocene compounds, the central metal is coordinated with one or more π-bonded ligands, usually cyclopentadienyl moieties, and with one or more sigma-bonded ligands. The latter are usually halogen, preferably chlorine. In the usual process for preparing dihalide metallocene compounds the lithium salts of the ligands are contacted with a tetrahalide of the metal. This process generates LiCl as a by-product that is difficult to separate because of the low solubility of the dihalide metallocene compounds in the usual solvents, and often the yield of the process is not satisfactory.

For instance, F. Wild et al. (*J. Organomet. Chem.*, 288: 63–67, 1985) describe the synthesis of chiral ansa-zirconocene derivatives with ethylene-bridged ligands. In particular, it is reported the preparation of ethylene-bis(1-indenyl)zirconium dichloride by reaction of the dilithium salt of bis(1-indenyl)ethane with $ZrCl_4$, in a yield of about 35%. Better results have been obtained by I. M. Lee et al. (*Organometallics*, 11:2115–2122, 1992), who prepared ethylene-bis(1-indenyl)zirconium dichloride in a yield of 52%. Another example can be found in Polyhedron 1990, 9, 301 wherein it is reported the synthesis of bis(indenyl)zirconium dichloride starting from indene and zirconium tetrachloride with a final yield of 58%.

In Izv. Akad. Nauk SSSR, Ser. Khim. 1976, 2621 there is described a reaction of mercury chloride ($HgCl_2$) with bis(cylopentadienyl)zirconium dibenzyl. In this paper it is shown that, instead of the expected bis(cylopentadienyl)zirconium dichloride, the reaction product is the complex $(C_5H_5)_2ZrCl_2 \cdot 3C_6H_5CH_2HgCl$.

In Dokl. Akad. Nauk SSSR (1976), 231(1), 114–15, G. A. Razuvaev investigates the mechanism of photo or thermo demethylation and dearylation by using bis(cylopentadienyl)zirconium dimethyl or dibenzyl and carbon tetrachloride or chloroform. The reaction is slow (about 100 h at 150° C. for the thermodemethylation) and moreover the yields are rather low.

A process for obtaining bis(cylopentadienyl)zirconium chloride methyl has been described by Wailes in Journal of Organometallic Chemistry 1972, 34, 155. According to this process, bis(cyclopentadienyl)zirconium chloride methyl is obtained by reacting the dimethyl derivative with $PbCl_2$. The yield of this process is not reported. The applicant by running a test according to the process described by Wailes (reported as comparative example 11) has found that that the yield of this process is not satisfactory for an industrial process.

Therefore it is felt the need for a simpler and more convenient and practical method to produce the above metallocene derivatives in satisfactory yields.

This need is fulfilled according to the present invention that, according to a first object, relates to a process for preparing dihalide or monohalide metallocene compounds of formula (I):

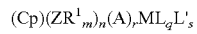

$$(Cp)(ZR^1{}_m)_n(A)_rML_qL'_s \qquad (I)$$

wherein $(ZR^1{}_m)_n$ is a divalent group bridging the Cp and A moieties; Z being C, Si, Ge, N or P, and the $R^1$ groups, equal to or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups, optionally containing one or more heteroatoms belonging to groups 13–17 of the Periodic Table of the Elements, or two $R^1$ can form an aliphatic or aromatic $C_4$–$C_7$ ring that can bear substituents;

Cp is an unsubstituted or substituted cyclopentadienyl group, optionally condensed to one or more unsubstituted or substituted, saturated, unsaturated or aromatic rings, containing from 4 to 6 carbon atoms, optionally containing one or more heteroatoms belonging to groups 13–17 of the Periodic Table of the Elements;

A is O, S, $NR^2$ or $PR^2$, $R^2$ being hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp;

M is zirconium, titanium or hafnium, preferably being zirconium or hafnium;

the L substituents, equal to or different from each other, preferably equal, are chlorine, bromine, iodine, preferably chlorine;

L' is selected from the group consisting of hydrogen, a linear or branched, saturated or unsaturated $C_1$–$C_{20}$ allyl, $C_3$–$C_{20}$ cycloalkyl, $Q$-$C_{2\text{-}0}$ aryl, $C_7$–$C_{20}$ alkylaryl or $C_7$–$C_{20}$ arylalkyl group, optionally containing one or more Si or Ge atoms; preferably L' is methyl, ethyl, n-butyl, sec-butyl, phenyl, benzyl or —$CH_2Si(CH_3)_3$; more preferably L' is methyl;

m is 1 or 2 depending on the oxidation state of Z, more specifically it is 1 when Z is N or P, and it is 2 when Z is C, Si or Ge;

n is 0, 1, 2, 3 or 4, preferably it is 0, 1 or 2; being 0 when r is 0 or 2;

r is 0, 1 or 2, preferably being 0 or 1;

q is 1, 2, or 3;

s is 0 or 1;

s and q satisfying the following equation: q+s=3-r, preferably q is 1 or 2 and s is 0 or 1; more preferably q is 2 and s is 0;

said process comprising contacting a compound of formula (II):

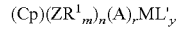

$$(Cp)(ZR^1{}_m)_n(A)_rML'_y \qquad (II)$$

wherein y is equal to s+q and Cp, Z, $R^1$, A, M, L', m, r, n, s and q have the same meaning as above, with an halogenating agent selected from the group consisting of $T^1L_w{}^1$, $T^2L_w{}^2$, O=$T^3L_w{}^3$, $R^6C(O)L$, $L_2$ and HL, mercury dichloride ($HgCl_2$) being excluded, wherein:

$T^1$ is a metal of groups 3–13 of the periodic table (new IUPAC version) or of the lanthanides series; preferably $T^1$ is a metal of groups 7–11 of the periodic table (new IUPAC version);

$T^2$ is a nonmetal element of groups 13–16 of the periodic table (new IUPAC version) with the exclusion of carbon;

$T^3$ is selected from the group consisting of C, P and S;

O is an oxygen atom bonded to $T^3$ through a double bond;

$R^6$ is selected from a linear or branched, saturated or unsaturated $C_1$–$C_{20}$ allyl, $C_3$–$C_{20}$ cycloalkyl, $C_6$–$C_{20}$ aryl, $C_7$–$C_{20}$ alkylaryl or $C_7$–$C_{20}$ arylalkyl;

L has the same meaning as above;

H is hydrogen;

$w^1$ is equal to the oxidation state of the metal $T^1$;

$w^2$ is equal to the oxidation state of the element $T^2$;

$w^3$ is equal to the oxidation state of the element $T^3$ minus 2.

The compound of formula (II) are well know in the art for example they can be easily prepared as described in WO 99/36427 or WO 00/75151.

An alternative embodiment for preparing dihalide or monohalide metallocene compounds of formula (I) starting directly from the ligand without isolating the compound of formula (II) comprises the following steps:

a) reacting a ligand of formula (Y-Cp) $(ZR^1_m)_n(AY)_r$ or when n is 0 a mixture of ligands Y-Cp and r(A-Y) with an amount EQ of a compound of formula $L'_jB$ or L'MgL''' such that EQ≧1+r molar equivalents with respect to Cp, preferably 1+r≦EQ≦1+r+q molar equivalents; more preferably EQ=1+r+q molar equivalents, wherein Cp, A, Z, $R^1$, m, r, q, and L' have the meaning reported above; L''' is selected from the group consisting of chlorine, bromine, iodine; n is an integer having values 1, 2, 3 or 4; the groups Y, the same or different from each other, are suitable leaving groups; Mg is magnesium; B is an alkaline or alkaline-earth metal; and j is 1 or 2, j being equal to 1 when B is an alkali metal, and j being equal to 2 when B is an alkaline-earth metal;

b) reacting the product obtained from step a) with at least 1 molar equivalent with respect to Cp of a compound of formula ML''$_4$, wherein M have the meaning reported above, L'' is selected from the group consisting of chlorine, bromine, iodine;

c) if the amount EQ of a compound of formula $L'_jB$ or L'MgL'' added in step a) is less than 1+r+q, adding to the reaction mixture an amount of a compound of formula $L'_jB$ or L'MgL''' equal to or higher than 1+r+q−EQ molar equivalents, preferably equal to 1+r+q−EQ;

d) optionally purifying the mixture and separating the meso and the rac forms; and e) reacting the mixture with an halogenating agent selected from the group consisting of: $T^1L_{w'}^1$; $T^2L_{w'}^2$; $O=T^3L_{w'}^3$; $R^6C(O)L$; $L_2$ and HL wherein $T^1$, $T^2$, $T^3$, L, $w^1$, $w^2$, $w^3$ and $R^6$ have been described above.

When n is different from 0 and r is 1 a preferred process for preparing the dihalide or monohalide of bridged metallocene compounds of formula (III)

$$(Cp)(ZP^1_m)_n(A)ML_qL'_s \quad \text{(III)}$$

wherein M, Cp, A, Z, $R^1$, m, q, s, L and L' have the meaning reported above and n is an integer having values 1, 2, 3 or 4; comprises the following steps:

a) reacting a ligand of formula $(Y-Cp)(ZR^1_m)_n(A-Y)$ with at least 2+q molar equivalents with respect to Cp, of a compound of formula $L'_jB$ or L'MgL''', wherein Cp, A, Z, $R^1$, m, q, and L' have the meaning reported above; L''' is selected from the group consisting of chlorine, bromine, iodine; n is an integer having values 1, 2, 3 or 4; the groups Y, the same or different from each other, are suitable leaving groups; Mg is magnesium; B is an alkaline or alkaline-earth metal; and j is 1 or 2, j being equal to 1 when B is an alkali metal, and j being equal to 2 when B is an alkaline earth metal; and b) reacting the product obtained from step a) with at least 1 molar equivalent of a compound of formula ML''$_4$, wherein M have the meaning reported above, L'' is selected from the group consisting of chlorine, bromine, iodine;

c) optionally purifying the mixture and separating the racemic and the meso forms;

d) reacting the mixture with an halogenating agent selected from the group consisting of: $T^1L_{w'}^1$; $T^2L_{w'}^2$; $O=T^3L_{w'}^3$; $R^6C(O)L$; $L_2$ and HL wherein $T^1$, $T^2$, $T^3$, L, $w^1$, $w^2$, $w^3$ and $R^6$ have been described above.

When A is equal to Cp and n is equal to 0 a preferred process for preparing metallocene compounds of formula (IV)

$$(Cp)(Cp)_rML_qL'_s \quad \text{(IV)}$$

wherein M, Cp, M, L, L', r, q and s have been described above comprises the following steps:

a) reacting 1+r molar equivalent of a ligand of formula (Y-Cp) with at least 3+r molar equivalents of a compound of formula $L_jB$ or L'''MgL', wherein Cp, L''' and L' have the meaning reported above; the groups Y, the same or different from each other, are suitable leaving groups; B is an alkaline or alkaline-earth metal; and j is 1 or 2, j being equal to 1 when B is an alkali metal, and j being equal to 2 when B is an alkaline-earth metal;

b) reacting the product obtained from step a) with at least 1 molar equivalent of a compound of formula ML''$_4$, wherein M have the meaning reported above, L'' is selected from the group consisting of chlorine, bromine, iodine;

c) optionally purifying the mixture; and d) reacting the mixture with an halogenating agent selected from the group consisting of: $T^1L_{w'}^1$; $T^2L_{w'}^2$; $O=T^3L_{w'}^3$; $R^6C(O)L$; $L_2$ and HL wherein $T^1$, $T^2$, $T^3$, L, $w^1$, $w^2$, $w^3$, $R^6$ have been described above.

According to a preferred embodiment of the present invention, all the reactions of the above processes are carried out in an aprotic solvent, either polar or apolar. Said aprotic solvent is preferably an aromatic or aliphatic hydrocarbon, optionally halogenated, or an ether, more preferably it is selected from the group consisting of benzene, toluene, pentane, hexane, heptane, cyclohexane, dichloromethane, diethylether, tetrahydrofurane or mixtures thereof.

The amount of the halogenating agent to be used depends from the type of compound. As a rule, for obtaining a monohalide metallocene compounds at least half molar equivalent with respect to the halogen atom has to be used, while for obtaining a dihalide derivative at least one molar equivalent with respect to the halogen atom has to be used. Excess of halogenating agent can also be used.

The Y leaving group is preferably hydrogen.

The ML''$_4$ reactant, is preferably selected from the group consisting of TiCl$_4$, ZrCl$_4$, HfCl$_4$. It can be used even in the form of a stabilized derivative, such as an etherate complex of ML''$_4$, easily available on the market.

The compounds $L'_jB$ and L'''MgL' are alkylating agents. Preferably L' is selected from the group consisting of methyl, ethyl, n-butyl, sec-butyl, phenyl, benzyl and —CH$_2$Si(CH$_3$)$_3$. More preferably L' is methyl.

In the compound $L_jB$, B is an alkali or alkaline-earth metal, preferably Li or Mg; j can be 1 or 2, as already reported.

The compound L'''MgL' is a Grignard reagent, wherein Mg is magnesium and L''' and L' have the meanings reported above. L''' is preferably bromine or iodine.

According to a preferred embodiment of the process of the invention, said alkylating agent is methyllithium.

Preferably in the processes for preparing compounds of formula (I), (III) and (IV) in step (a), the ligands are previously dissolved in an aprotic polar solvent and to the resulting solution is added the alkylating agent $L'_jB$ or L'''MgL'. This addition is preferably carried out at a temperature ranging from −100° C. to +80° C., more preferably from −80° C. to +10° C., over a period of 5 to 45 minutes, more preferably of 10 to 20 minutes. The alkylating agent is preferably added in the form of a solution in one of the above mentioned aprotic solvents, preferably dropwise.

The thus obtained reaction mixture is preferably allowed to react, under stirring, for a period ranging from 1 to 6 hours, more preferably from 2 to 3 hours, at a temperature comprised between −10° C. and +80° C., more preferably at room temperature.

Before the reaction with $ML''_4$, in step (b), the mixture obtained from step (a) is preferably cooled to a temperature ranging from −100° C. to +80° C., more preferably from −80° C. to +70° C. Then $ML''_4$ is quickly added to the cooled slurry in the form of a solution in one of the above mentioned aprotic solvents, preferably pentane, hexane, heptane or toluene.

The reaction mixture is then allowed to react for a period ranging from 10 minutes to 36 hours, more preferably from 1 to 18 hours, at a temperature comprised between −100° C. and +80° C., more preferably between −50° C. and +50° C., even more preferably at room temperature.

In the halogenating step the temperature ranges from −50° C. to +150° C., preferably from 0° C. to 100° C., more preferably from 20° C. to 50° C. The halogenating agent is generally added dropwise and then the reaction mixture is preferably allowed to react, under stirring, for a period ranging from 1 to 6 hours, more preferably from 2 to 3 hours, at a temperature comprised between −10° C. and +80° C., more preferably at room temperature.

The thus obtained metallocene compounds of formulas (I), (III) and (IV) can be isolated according to the common procedures known in the state of the art.

Non limiting examples of halogenating agents of formula $T^1L_{w'}^1$ are: $FeCl_3$, $CuCl_2$ and $ZnCl_2$.

Non limiting examples of halogenating agents of formula $T^2L_{w'}^2$ are: $BCl_3$, $BBr_3$, $SiCl_4$ and $PCl_5$.

Non limiting examples of halogenating agents of formula $O=T^3L_{w'}^3$ are: $SOCl_2$ and $POCl_3$.

Non limiting examples of halogenating agents of formula $R^6C(O)L$ are: $CH_3C(O)Cl$, $C_6H_5CH_2C(O)Cl$, $C_6H_5C(O)Cl$ and $CH_3CH_2CH_2C(O)Cl$.

Non limiting examples of halogenating agents of formula $L_2$ are: $Br_2$, $Cl_2$ and $I_2$.

Non limiting examples of halogenating agents of formula $HL$ are $HCl$, $HBr$ and $HI$.

In the optional steps (c) and (d) the purification of the reaction mixture is preferably carried out by simply filtering the solution in order to remove the salts. Also other systems of purification can be used, for example a suitable solvent in order to precipitate the undesired by products can be added with subsequently filtration. In these steps it is also possible to separate (when present) the racemic and the meso form by using methods known in the art. For example, by using suitable solvents it is possible to precipitate one form with subsequently filtration. All the operations are carried out in inert atmosphere.

In the metallocenes of formula (I) and (III), the divalent bridge $(ZR^1_m)_n$ is preferably selected from the group consisting of $CR^1_2$, $(CR^1_2)_2$, $(CR^1_2)_3$, $SiR^1_2$, $GeR^1_2$, $NR^1$ and $PR^1$, $R^1$ having the meaning reported above. More preferably, said divalent bridge is $Si(CH_3)_2$, $SiPh_2$, $CH_2$, $(CH_2)_2$, $(CH_2)_3$ or $C(CH_3)_2$.

The variable m is 1 or 2; the variable n ranges from 0 to 4 preferably is 1 or 2, when n>1, the atoms Z can be the same or different from each other, such as in divalent bridges $-CH_2-O-$, $-CH_2-S-$ and $-CH_2-Si(CH_3)_2-$. When n=0 and r=1, A can have only the meaning of Cp.

In the metallocenes of formula (I), (III) and (IV) the ligand Cp, which is π-bonded to said metal M, is preferably selected from the group consisting of cyclopentadienyl; mono-, di-, tri- and tetra-methyl cyclopentadienyl; 4-tertbutyl-cyclopentadienyl; 4-adamantyl-cyclopentadienyl; indenyl; mono-, di-, tri- and tetra-methyl indenyl; 4,5,6,7-tetrahydroindenyl; fluorenyl; 5,10-dihydroindeno[1,2-b]indol-10-yl; N-methyl- or N-phenyl-5,10-dihydroindeno [1,2-b] indol-10-yl; 5,6-dihydroindeno[2,1-b]indol-6-yl; N-methyl- or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl and 2,5-dimethyl-cyclopenta[1,2-b:4,3-b']-dithiophene.

The group A has preferably the same meaning of Cp, or it is N-methyl, N-ethyl, N-isopropyl, N-butyl, N-phenyl, N-benzyl, N-cyclohexyl and N-cyclododecyl.

Non limiting examples of metallocene compounds of formula (I), (III) and (IV) are the racemic and the meso form (when present) of the following compounds:
bis(cyclopentadienyl)zirconium dichloride;
bis(indenyl)zirconium dichloride;
bis(tetrahydroindenyl)zirconium dichloride;
bis(fluorenyl)zirconium dichloride;
dimethylsilanediylbis(indenyl)zirconium dichloride,
dimethylsilanediylbis(2-methyl-4-phenylindenyl)zirconium dichloride,
dimethylsilanediylbis(4-naphthylindenyl)zirconium dichloride,
dimethylsilanediylbis(2-methylindenyl)zirconium dichloride,
dimethylsilanediylbis(2-methyl-(4-t-butyl-phenyl) indenyl) zirconium dichloride,
dimethylsilanediylbis(2-methyl-4-isopropylindenyl)zirconium dichloride,
dimethylsilanediylbis(2,4-dimethylindenyl)zirconium dichloride,
dimethylsilanediylbis(2-methyl-4,5-benzoindenyl)zirconium dichloride,
dimethylsilanediylbis(2,4,7-trimethylindenyl)zirconium dichloride,
dimethylsilanediylbis(2,4,6-trimethylindenyl)zirconium dichloride,
dimethylsilanediylbis(2,5,6-trimethylindenyl)zirconium dichloride,
methyl(phenyl)silanediylbis(2-methyl-4,6-diisopropylindenyl)-zirconium dichloride,
methyl(phenyl)silanediylbis(2-methyl-4-isopropylindenyl)-zirconium dichloride,
1,3-propylenebis(indenyl)zirconium dichloride,
1,3-propylenebis(4,7-dimethylindenyl)zirconium dichloride,
1,3-propylenebis(2-methyl-4-phenylindenyl)zirconium dichloride,
1,3-propylenebis(2-methyl-4,6-diisopropylindenyl)zirconium dichloride,
1,3-propylenebis (2-methyl-4,5-benzoindenyl)zirconium dichloride,
1,2-ethylenebis(indenyl)zirconium dichloride,
1,2-ethylenebis(4,7-dimethylindenyl)zirconium dichloride,
1,2-ethylenebis(2-methyl-4-phenylindenyl)zirconium dichloride,
1,4-butanediylbis(2-methyl-4-phenylindenyl)zirconium dichloride,
1,2-ethylenebis(2-methyl-4,6-diisopropylindenyl)zirconium dichloride, 1,4-butanediylbis(2-methyl-4-isopropylindenyl)zirconium dichloride,
1,4-butanediylbis(2-methyl-4,5-benzoindenyl)zirconium dichloride,
1,2-ethylenebis (2-methyl-4,5-benzoindenyl)zirconium dichloride,
[4-($\eta^5$-cyclopentadienyl)-4,6,6-trimethyl($\eta^5$-4,5-tetrahydropentalene)]dichloridezirconium,
[4-($\eta^5$-3'-trimethylsilylcyclopentadienyl)-4,6,6-trimethyl ($\eta^5$-4,5-tetrahydropentalene)]dichloridezirconium,
(tert-butylamido)(tetramethyl-$\eta^5$-cyclopentadienyl)-1,2-ethane-dichloridetitanium,
(methylamido)(tetramethyl-$\eta^5$-cyclopentadienyl)dimethylsilyl-dichloridetitanium,
(methylamido)(tetramethyl-$\eta^5$-cyclopentadienyl)-1,2-ethanediyl-dichloridetitanium,
(tertbutylamido)-(2,4-dimethyl-2,4-pentadien-1-yl)dimethylsilyl-dichloridetitanium,
bis(1,3-dimethylcyclopentadienyl)zirconium dichloride,
methylene(3-methyl-cyclopentadienyl)-7-(2,5-dimethylcyclopentadienyl-[1,2-b:4,3-b']dithiophene)zirconium dichloride;
methylene(3-isopropyl-cyclopentadienyl)-7-(2,5-dimethylcyclopentadienyl-[1,2-b:4,3-b']dithiophene)zirconium dichloride;
methylene(2,4-dimethyl-cyclopentadienyl)-7-(2,5-dimethylcyclopentadienyl-[1,2-b:4,3-b']dithiophene)zirconium dichloride;
methylene(2,3,5-trimethyl-cyclopentadienyl)-7-(2,5-dimethylcyclopentadienyl-[1,2-b:4,3-b']dithiophene)zirconium dichloride;
methylene-1-(indenyl)-7-(2,5-dimethylcyclopentadienyl-[1,2-b:4,3-b']dithiophene)zirconium dichloride;
methylene-1-indenyl)-7-2,5-ditrimethylsilylcyclopentadienyl-[1,2-b:4,3-b']dithiophene)zirconium dichloride;
methylene-1-(3-isopropyl-indenyl)-7-(2,5-dimethylcyclopentadienyl-[1,2-b:4,3-b']dithiophene)zirconium dichloride;
methylene-1-(2-methyl-indenyl)-7-(2,5-dimethylcyclopentadienyl-[1,2-b:4,3-b']dithiophene)zirconium dichloride;
methylene-1-(tetrahydroindenyl)-7-(2,5-dimethylcyclopentadienyl-[1,2-b:4,3-b']dithiophene)zirconium dichloride;
methylene(2,4-dimethyl-cyclopentadienyl)-7-2,5-dimethylcyclopentadienyl-[1,2-b:4,3-b']dioxazol)zirconium dichloride;
methylene(2,3,5-trimethyl-cyclopentadienyl)-7-2,5-dimethylcyclopentadienyl-[1,2-b:4,3-b']dioxazol)zirconium dichloride;
methylene-1-(indenyl)-7-(2,5-dimethylcyclopentadienyl-[1,2-b:4,3-b']dioxazol)zirconium dichloride;
isopropylidene(3-methyl-cyclopentadienyl)-7-2,5-dimethylcyclopentadienyl-[1,2-b:4,3-b') dithiophene)zirconium dichloride;
isopropylidene(2,4-dimethyl-cyclopentadienyl)-7-(2,5-dimethylcyclopentadienyl-[1,2-b:4,3-b'] dithiophene)zirconium dichloride;
isopropylidene(2,4-diethyl-cyclopentadienyl)-7-(2,5-dimethylcyclopentadienyl-[1,2-b:4,3-b']dithiophene)zirconium dichloride;
isopropylidene(2,3,5-trimethyl-cyclopentadienyl)-7-(2,5-dimethylcyclopentadienyl-[1,2-b:4,3-b']dithiophene)zirconium dichloride;
isopropylidene-1-(indenyl)-7-(2,5-dimethylcyclopentadienyl-[1,2-b:4,3-b']dithiophene)zirconium dichloride;
isopropylidene-1-(2-methyl-indenyl)-7-(2,5-dimethylcyclopentadienyl-[1,2-b:4,3-b']dithiophene)zirconium dichloride;
dimethylsilandiyl-1-(2-methyl-indenyl)-7-(2,5-dimethylcyclopentadienyl-[1,2-b:4,3-b']dithiophene)hafnium dichloride;
dimethylsilanediyl(3-tert-butyl-cyclopentadienyl)(9-fluorenyl)zirconium dichloride,
dimethylsilanediyl(3-isopropyl-cyclopentadienyl)(9-fluorenyl)zirconium dichloride,
dimethylsilanediyl(3-methyl-cyclopentadienyl)(9-fluorenyl)zirconium dichloride,
dimethylsilanediyl(3-ethyl-cyclopentadienyl)(9-fluorenyl) zirconium dichloride,
1-2-ethane(3-tert-butyl-cyclopentadienyl)(9-fluorenyl)zirconium dichloride,
1-2-ethane (3-isopropyl-cyclopentadienyl)(9-fluorenyl)zirconium dichloride,
1-2-ethane (3-methyl-cyclopentadienyl)(9-fluorenyl)zirconium dichloride,
1-2-ethane (3-ethyl-cyclopentadienyl)(9-fluorenyl)zirconium dichloride,
dimethylsilandiylbis-6-(3-methylcyclopentadienyl-[1,2-b]-thiophene) zirconium dichloride;
dimethylsilandiylbis-6-(4-methylcyclopentadienyl-[1,2-b]-thiophene)zirconium dichloride;
dimethylsilandiylbis-6-(4-isopropylcyclopentadienyl-[1,2-b]-thiophene)zirconium dichloride;
dimethylsilandiylbis-6-(4-ter-butylcyclopentadienyl-[1,2-b]-thiophene)zirconium dichloride;
dimethylsilandiylbis-6-(3-isopropylcyclopentadienyl-[1,2-b]-thiophene)zirconium dichloride;
dimethylsilandiylbis-6-(3-phenylcyclopentadienyl-[1,2-b]-thiophene)zirconium dichloride;
dimethylsilandiylbis-6-(2,5-dimethyl-3-phenylcyclopentadienyl-[1,2-b]-thiophene)zirconium dichloride;
dimethylsilandiylbis-6-[2,5-dimethyl-3-(2-methylphenyl) cyclopentadienyl-(1,2-b]-thiophene]zirconium dichloride;
dimethylsilandiylbis-6-[2,5-ethyl-3-(2,4,6-trimethylphenyl) cyclopentadienyl-[1,2-b]-thiophene]zirconium dichloride;
dimethylsilandiylbis-6-[2,5-dimethyl-3-mesitylenecyclopentadienyl-[1,2-b]-thiophene]zirconium dichloride;
dimethylsilandiylbis-6-(2,4,5-trimethyl-3-phenylcyclopentadienyl-[1,2-b]-thiophene)zirconium dichloride;
dimethylsilandiylbis-6-(2,5-diethyl-3-phenylcyclopentadienyl-[1,2-b]-thiophene)zirconium dichloride;
dimethylsilandiylbis-6-(2,5-diisopropyl-3-phenylcyclopentadienyl-[1,2-b]-thiophene)zirconium dichloride;
dimethylsilandiylbis-6-(2,5-diter-butyl-3-phenylcyclopentadienyl-[1,2-b]-thiophene)zirconium dichloride;
dimethylsilandiylbis-6-(2,5-ditrimethylsilyl-3-phenylcyclopentadienyl-[1,2-b]-thiophene)zirconium dichloride;
dimethylsilandiylbis-6-(3-methylcyclopentadienyl-[1,2-b]-silole)zirconium dichloride;
dimethylsilandiylbis-6-(3-isopropylcyclopentadienyl-[1,2-b]-silole)zirconium dichloride;
dimethylsilandiylbis-6-(3-phenylcyclopentadienyl-[1,2-b]-silole)zirconium dichloride;
dimethylsilandiylbis-6-(2,5-dimethyl-3-phenylcyclopentadienyl-[1,2-b]-silole)zirconium dichloride;
dimethylsilandiylbis-6-[2,5-dimethyl-3-2-methylphenyl)cyclopentadienyl-[1,2-b]-silole]zirconium dichloride;
dimethylsilandiylbis-6-[2,5-dimethyl-3-(2,4,6-trimethylphenyl)cyclopentadienyl-[1,2-b]-silole]zirconium dichloride;
dimethylsilandiylbis-6-[2,5-dimethyl-3-mesitylenecyclopentadienyl-[1,2-b]-silole]zirconium dichloride;

dimethylsilandiylbis-6-(2,4,5-trimethyl-3-phenylcyclopentadienyl-[1,2-b]-silole)zirconium dichloride;
[dimethylsilyl(tert-butylamido)][(N-methyl-1,2-dihydrocyclopenta[2,1-b]indol-2-yl)]titanium dichloride;
[dimethylsilyl(tert-butylamido)][(6-methyl-N-methyl-1,2-dihydrocyclopenta[2,1-b]indol-2-yl)]titanium dichloride;
[dimethylsilyl(tert-butylamido)][(6-methoxy-N-methyl-1,2-dihydrocyclopenta[2,1-b]indol-2-yl)]titanium dichloride;
[dimethylsilyl(tert-butylamido)][(N-ethyl-1,2-dihydrocyclopenta[2,1-b]indol2-yl)]titanium dichloride;
[dimethylsilyl(tert-butylamido)][(N-phenyl-1,2-dihydrocyclopenta[2,1-b]indol2-yl)]titanium dichloride;
[dimethylsilyl(tert-butylamido)][(6-methyl-N-phenyl-1,2-dihydrocyclopenta[2,1-b]indol2-yl)]titanium dichloride;
[dimethylsilyl(tert-butylamido)][(6-methoxy-N-phenyl-1,2-dihydrocyclopenta[2,1-b]indol2-yl)]titanium dichloride;
[dimethylsilyl(tert-butylamido)][(N-methyl-3,4-dimethyl-1,2-dihydrocyclopenta[2,1-b]indol-2-yl)]titanium dichloride;
[dimethylsilyl(tert-butylamido)][(N-thyl-3,4-dimethyl-1,2-dihydrocyclopenta[2,1-b]indol-2-yl)]titanium dichloride;
[dimethylsilyl(tert-butylamido)][(N-phenyl-3,4-dimethyl-1,2-dihydroclopenta[2,1-b]indol-2-yl)]titanium dichloride;

as well as the correspondent titanium and hafnium compounds and the dibromide and diodide compounds.

The process according to the present inventions shows several advantages with respect to the processes generally known in the state of the art. The overall yields starting from the ligands are generally higher than those reported in the art. Moreover, it is easier to purify the desired product, due to the better solubility of the formed intermediate alkylated metallocene with respect to the dihalide or monohalide product. Further, because of the higher solubility of said intermediate metallocene it is also easy to separate the racemic and the meso form at this step and thus to obtain the substantially pure racemic or meso form as the final product.

The metallocene compounds obtained with the process according to the present invention, in combination with a suitable activator such as an alumoxane, can be used as a catalyst for the polymerization of olefins. Particularly, they can be used for the homo or co-polymerization of alpha-olefins of formula $CH_2=CHR$ wherein R is hydrogen or a $C_1$–$C_{20}$ alkyl, such as propylene, 1-butene, 1-pentene, 4-methyl-1-pentene, 1-hexene and 1-octene.

An interesting use is for the production of isotactic, syndiotactic or atactic polypropylene. Another interesting use is for the copolymerization of ethylene with alpha-olefins, such as propylene, 1-butene, 1-pentene, 4-methyl-1-pentene, 1-hexene and 1-octene, with cycloolefins, such as cyclopentene, cyclohexene, norbornene and 4,6-dimethyl-1-heptene, or with polyenes, such as 1,4-hexadiene, isoprene, 1,3-butadiene, 1,5-hexadiene and 1,6-heptadiene.

Further, they can be advantageously used in olefin oligomerization or hydrogenation reactions. The above metallocenes form suitable polymerization catalytic systems in association with alumoxanes of formula:

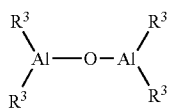

wherein the substituents $R^3$ can be a linear or branched, saturated or unsaturated, $C_1$–$C_{20}$ alkyl, alkenyl or alkylaryl radical;

or in association with the product obtained by contacting an organometallic aluminum compound of formula $AlR^5{}_{3-z}H_z$, wherein $R^5$ can be $C_1$–$C_{10}$ alkyl, alkenyl or alkylaryl radicals, optionally containing one or more Si or Ge atoms, with water.

Particularly suitable alumoxanes, acting as cocatalysts with the above metallocenes, are methylalumoxane (MAO), tris(2-methyl-propyl)alumoxane (TIB AO) and 2,4,4-trimethyl-pentylalumoxane (TIOAO).

Non-limiting examples of organometalic aluminum compounds that, upon contacting with water, produce suitable cocatalysts are trimethylaluminum (TMA), tris(2,4,4-trimethyl-pentyl)aluminum (TIOA), tris(2-methyl-propyl)aluminum (TIBA), tris(2,3,3-trimethyl-butyl)aluminum, tris(2,3-trimethyl-hexyl)aluminum, tris(2,3-dimethyl-butyl)aluminum, tris(2,3-dimethyl-pentyl)aluminum, tris(2,3-dimethyl-heptyl)aluminum, tris(2-methyl-3-ethyl-pentyl)aluminum and tris(2-ethyl-3,3-dimethyl-butyl).

The above catalysts can suitably be used on inert supports, such as silica, alumina, styrene/divinylbenzene copolymers, polyethylene or polypropylene, particularly for use in the gas phase polymerizations.

The olefin polymerization processes can be carried out in liquid phase, optionally in the presence of an inert hydrocarbon solvent, either aromatic (e.g. toluene) or aliphatic (e.g. propane, hexane, heptane, isobutane, cyclohexane and 2,2,4-trimethylpentane). The polymerization temperature generally ranges from about 0° C. to about 250° C., and preferably from 20 to 150° C.

The following examples are given for illustrative and not limitative purposes.

General Procedures and Characterizations

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. MeLi (Acros), $TiCl_4$ (Aldrich), $ZrCl_4$ (Aldrich), $HfCl_4$ (Roc-Ric, 99.99% Hf), $FeCl_3$ (Aldrich), $BCl_3$ (Aldrich), CuCl (Carlo Erba, RPE-ACS, 95%) and $SiCl_4$ (Aldrich) were used as received. Technical indene (Aldrich) was purified by passing over activated $Al_2O_3$; All compounds were analyzed on an AC 200 Bruker spectrometer, by $^1H$ NMR (200.13 MHz, $CD_2Cl_2$, referenced against the middle peak of residual $CHDCl_2$ at 5.35 ppm, or $C_6D_6$, referenced against the peak of residual $C_6D_5H$ at 7.15 ppm) and $^{13}C$ NMR (50.323 MHz, Broad Band Decoupling, $C_6D_6$, referenced to the central line of $C_6D_6$ at 128.00 ppm). All NMR solvents were dried over $P_4O_{10}$ or $CaH_2$ and distilled before use. GC-MS analyses were carried out on a HP 5890-series 2 gas-chromatograph and a HP 5970 mass spectrometer.

COMPARATIVE EXAMPLE 1

Synthesis of $Ind_2ZrCl_2$ 40 mL of a 1.5 M solution of BuLi in $Et_2O$ (60 mmol) were added dropwise to 7.0 mL of indene (60.0 mmol) in 20 mL of THF, cooled to −78° C. At the end of the addition, the solution was allowed to warm to room temperature and stirred for 1 hour, to give an orange solution. 7 g of $ZrCl_4$ (30.0 mmol) were dissolved in 30 mL of THF at −78° C. in a 100 mL flask equipped with reflux condenser (exothermic reaction). The mixture was allowed to reach room temperature with stirring, then refluxed for 30 min, to give a clear, brown solution. To this solution was added the THF solution of indenyllithium at room temperature with stirring, then the resulting suspension was stirred for two hours. The color turned yellow. The solvents were removed under reduced pressure, the residue slurried in $Et_2O$ and transferred into an extractor, washed with $Et_2O$ until colorless, then extracted with $CH_2Cl_2$, the extract dried and washed again with $Et_2O$ and then pentane, finally dried to give 4.35 g of yellow, analytically pure $Ind_2ZrCl_2$. Isolated yield 36.9%.

COMPARATIVE EXAMPLE 2

Synthesis of $Ind_2ZrCl_2$ 9.9 mL of a 1.6 M solution of MeLi in $Et_2O$ (15.8 mmol) were added dropwise to 1.97 g of technical indene (93.3% by GC, 15.8 mmol) in 30 mL of $Et_2O$, at the end of the addition the mixture was stirred for 40 min at room temp., then it was added at once to 1.84 g of $ZrCl_4$ (7.9 mmol) slurried in 30 mL of pentane, then the resulting suspension was stirred for two hours. The color turned yellow. The product in pentane/$Et_2O$ was transferred into an extractor, filtrated, the filtrate was discarded, the residue dried and extracted at reflux with 80 mL of $CH_2Cl_2$ for 5 hours. The extract was dried to give 2.08 g of lemon yellow $Ind_2ZrCl_2$, containing 4 mol % of $Ind_2ZrClMe$ ($^1H$ NMR). Isolated yield 67%.

EXAMPLE 3

Synthesis of $Ind_2ZrCl_2$

Synthesis of $Ind_2ZrMe_2$.

15.8 ml of a solution of MeLi 1.6 M in $Et_2O$ (25.3 mmol) were added at room temperature to a solution of 1.5 g (12.6 mmoles) of indene (Aldrich, 97.9% by G.C.) in 30 ml of $Et_2O$ in about 5 minutes (exothermic reaction). The mixture was stirred for 30 min, to give an orange solution. 1.47 g of $ZrCl_4$ (6.33 mmol) were slurried in 30 ml pentane. The $ZrCl_4$ slurry in pentane was quickly added to the Li salt solution in $Et_2O$ (exothermic reaction). The reaction mixture was stirred for 30 min, and the yellow-brown suspension was treated as described above, to give 1.92 g (86.5% yield) of a light yellow solid, which was characterized by $^1H$ NMR as spectroscopically pure $Ind_2ZrMe_2$.

Anal. Calcd for $C_{20}H_{20}Zr$: C, 68.32; H, 5.73; Zr, 25.94. Found: C, 67.3; H, 5.75; Cl, <0.05.

$^1$H-NMR ($C_6D_6$, δ, ppm): –0.50 (s, Ti—$CH_3$, 6H), 5.37 (t, Cp-H(2), 2H, J=3.24 Hz), 5.78 (d, Cp-H(1,3), 4H, J=3.24 Hz), 6.90–6.95 (m, Ar, 4H), 7.16–7.22 (m, Ar, 4H).

Synthesis of $Ind_2ZrCl_2$.

0.33 g of $Ind_2ZrMe_2$ (0.94 mmol) were charged in a 10 mL Schlenk tube, and dissolved in 4 mL of $CD_2Cl_2$. 0.485 g of CuCl (Carlo Erba, 95%, 4.65 mmol) were added, and the mixture stirred at room temperature for 6 hours, when $^1H$ NMR showed the reaction to be complete. 20 mL of $CH_2Cl_2$ were added and the mixture was filtered over a G4 frit The yellow-green solution was brought to dryness to give 0.34 g of yellow-green powder (yield 93%) whose $^1H$ NMR is identical to that of a true sample of $Ind_2ZrCl_2$.

$^1$H NMR ($CD_2Cl_2$, δ, ppm): 6.23 (d, H(1-3), 4H, J=3.32 Hz), 6.55 (t, H(2), 2H, J=3.32 Hz), 7.28–7.37 (m, Ar, 4H), 7.60–7.69 (m, Ar, 4H).

EXAMPLE 4

Synthesis of $Ind_2ZrCl_2$ 2.5 g of indene (92% wt by GC, 19.8 mmol) were dissolved in 30 mL of $Et_2O$ in a 250 mL Schlenk tube. 24.8 mL of MeLi 1.6 M in $Et_2O$ (39.7 mmol) were added with stirring at room temperature (exothermic reaction). After stirring for 40 min, a yellow-orange solution was obtained, to which was added a suspension of 2.3 g of $ZrCl_4$ (9.9 mmol) in 40 mL of pentane (exothermic reaction, the mixture turns dark brown). The mixture was stirred at room temperature for two hours, then concentrated under reduced pressure to give a black powder, which was slurried in 50 mL of $CH_2Cl_2$, cooled to 0° C., and added of 9.9 mL of $BCl_3$ 1M in heptane (9.9 mmol). During the addition, the mixture turns from dark grey to dark green. This was allowed to warm to room temperature and stirred for 30 min at room temperature (complete conversion to the dichloride observed by $^1H$ N at this time), then filtered and extracted with the same $CH_2Cl_2$ for 8 hours on a continuous extractor (the product precipitates in part as a yellow solid during extraction), the extract concentrated under reduced pressure to give a yellow powder, 3.74 g (96% yield based on Zr) of spectroscopically pure $Ind_2ZrCl_2$.

EXAMPLE 5

Synthesis of $Ind_2ZrCl_2$ 0.25 g of $Ind_2ZrMe_2$ (0.71 mmol) were dissolved in 10 mL of $CH_2Cl_2$ in a 25 mL Schlenk tube, and 0.71 mL of $BCl_3$ 1M in heptane (0.71 mmol) were added, a yellow precipitate start forming, and the slurry was stirred at room temperature for 1 hour, when $^1H$ NMR showed the conversion to $Ind_2ZrCl_2$ to be quantitative. The yellow suspension was brought to dryness to give 0.27 g of yellow, powdery, analytically pure $Ind_2ZrCl_2$ (yield 97%). Its $^1H$ NMR is identical to that of a true sample of $Ind_2ZrCl_2$.

EXAMPLE 6

Synthesis of $Ind_2ZrCl_2$ 0.172 g of $Ind_2ZrMe_2$ (0.49 mmol) were slurried in 5 mL of hexanes in a 10 mL Schlenk tube, and 0.49 mL of $BCl_3$ 1M in heptane (0.49 mmol) were added at room temperature, and the mixture stirred for 2 hours, to give a 45:55 mixture of $Ind_2ZrCl_2$ and $Ind_2ZrClMe$ ($^1H$ NMR), additional 0.3 mL of $BCl_3$ 1M in heptane (0.3 mmol) and sirred for additional 2 hours. At this point the reaction is complete and the product is analytically pure by $^1H$ NMR.

EXAMPLE 7

Synthesis of $Ind_2ZrCl_2$ 300 mg of $Ind_2ZrMe_2$ (20790/21, 0.85 mmol) were dissolved in 20 mL of $Et_2O$ in a 50 mL Schlenk tube. 0.95 mL of a 2M solution of HCl in $Et_2O$ (Aldrich, 1.71 mmol) were added at room temperature. Gas evolution ($CH_4$) is observed, together with instantaneous formation of a yellow precipitate. Removing the solvent under reduced pressure gives 320 mg of pure $Ind_2ZrCl_2$, yield 96%.

EXAMPLE 8

Synthesis of Ind$_2$ZrMeCl 380 mg of Ind$_2$ZrMe$_2$ (20790/21, 1.08 mmol) were dissolved in 5 mL of CH$_2$Cl$_2$ in a 10 mL Schlenk tube. 175 mg of anhydrous FeCl$_3$ (Aldrich, 99.9%, 1.08 mmol) were added at room temperature (immediate darkening to black), and then the mixture is heated at 40° C. for 6 hours. After 3 hours $^1$H NMR shows the presence of a 98:2 mixture of Ind$_2$ZrClMe and residual Ind$_2$ZrMe$_2$ (yield of Ind2ZrMeCl 98%).

EXAMPLE 9

Synthesis of Ind$_2$ZrI$_2$ 164 mg of of Ind$_2$ZrMe$_2$ (0.46 mmol) were dissolved in 2 mL of CD$_2$Cl$_2$ in a 10 mL Schlenk tube. 120 mg of I$_2$ crystals (0.47 mmol) were added at room temperature. The solution was warmed to 40° C. After 5 min stirring the I$_2$ is fully solubilized, to give a bright orange solution that was stirred for 6 hours at 40° C. $^1$H-NMR analysis shows the presence of residual Ind$_2$ZrMe$_2$, and the two reaction products Ind$_2$ZrIMe and Ind$_2$ZrI$_2$, in the ratio 6:67:27.

Additional 60 mg of I$_2$ were added, and the solution stirred at room temperature for 72 hours.

$^1$H-NMR analysis shows conversion to the target Ind$_2$ZrI$_2$.

Ind$_2$ZrIMe: $^1$H-NMR (CD$_2$Cl$_2$, δ, ppm): −1.47 (s, 3H, Zr—CH$_3$), 6.09 (t, 2H, Cp-H2, J=3.52 Hz), 6.39 (m, 2H, Cp-H(1,3)), 6.54 (m, 2H, Cp-H(3,1)), 7.23–7.28 (m, 2H, Ar), 7.64–7.69 (m, 2H, Ar).

Ind$_2$ZrI$_2$: $^1$H-NMR (CD$_2$Cl$_2$, δ, ppm): 2.19 (CH$_3$I, cfr. CH$_3$I in CDCl$_3$=2.16 ppm); 6.42 (d, Cp-H(1,3), 4H, J=3.33), 6.64 (t, Cp-H(2), 2H, J=3.33), 7.30–7.40 (m, Ar, 4H), 7.66–7.75 (m, Ar, 4H.

EXAMPLE 10

Synthesis of Ind$_2$TiClMe

Synthesis Ind$_2$TiMe$_2$ 31.0 mL of MeLi 1.6 M in Et$_2$O (49.6 mmol) were added with stirring at room temperature to a solution of 3 g of indene (94% by G.C., 24.3 mmol) in 30 mL of diethyl ether over a period of about 10 minutes (exothermic reaction). The Schlenk tube was kept in a water bath to remove the heat of reaction. The reaction mixture was stirred for 30 minutes. After this time the solution turned from light yellow to orange. 1.34 mL of TiCl$_4$ (99%, 12.2 mmol) were dissolved in 30 mL of pentane, and this solution was quickly added to the Li salt solution (exothermic reaction). The reaction mixture was stirred for two hours at room temperature with final formation of a dark brown suspension. The solvents were then removed under reduce pressure. The brown solid obtained was extracted in a Soxhlet apparatus with 80 mL of pentane. The filtrate was evaporated to dryness under reduced pressure to give 2.62 g of a yellow-brown powder (70% metal-based yield).

Anal. Calcd for C$_{20}$H$_{20}$Ti: C, 77.93; H, 6.54; Ti, 15.53. Found: C, 74.7; H, 6.35; Ti, 14.6; Cl, <0.05.

$^1$H-NMR (C$_6$D$_6$, δ, ppm): −0.50 (s, Ti—CH$_3$, 6H), 5.37 (t, Cp-H(2), 2H, J=3.24 Hz), 5.78 (d, Cp-H(1,3), 4H, J=3.24 Hz), 6.90–6.95 (m, Ar, 4H), 7.16–7.22 (m, Ar, 4H)

Synthesis Ind$_2$TiClMe 0.43 g of Ind2TiMe2 (20790/77, 1.4 mmol) were dissolved in 15 mL of toluene in a 50 mL Schlenk. 0.32 mL of SiCl$_4$ (99%, 2.79 mmol) were added at room temperature and the solution warmed up to 50° C. and stirred for 3 hours. $^1$H NMR reveals the formation of a 70:30 mixture of Ind$_2$TiClMe and Ind$_2$TiMe$_2$. To bring the reaction to completion, another 2 molar equivalents of SiCl4 (0.32 mL) were added, and the red-orange solution stirred for 3 additional hours at 50 0C, then dried, to give a quantitative yield of Ind2TiClMe as a brick red powder.

$^1$H-NMR (C$_6$D$_6$, δ, ppm): −0.08 (s, Ti—CH$_3$, 3H), 5.52 (t, Cp-H(2), 2H, J=3.33 Hz), 5.80 (ddd, Cp-H(1 or 3), 2H, J=0.88, 1.96, 3.33 Hz), 5.86 (ddd, Cp-H(3 or 1), 2H, J=0.88, 1.96, 3.33 Hz), 6.85–7.31 (m, Ar, 8H).

COMPARATIVE EXAMPLE 11

Synthesis of Ind$_2$ZrClMe

A slurry of 2.53 g of PbCl$_2$ (Aldrich, MW=278.106, 9.10 mmol) in 15 mL of toluene was added to a solution of Ind$_2$ZrMe$_2$ (1.25 g, MW=351.594, 3.56 mmol) in 35 mL of toluene, in a 100 mL Schlenk flask. The dark orange suspension obtained was stirred 38 hours at room temperature and 10 hours at 40–45° C., during which time formation of a black powder was observed. The suspension was then filtered on 4 frit and the filtrate was evaporated to dryness under reduced pressure to give 1.1 g of a dark yellow powder, which was characterized by $^1$H NMR as a mixture of Ind$_2$ZrMeCl and Ind$_2$ZrCl$_2$ in the ratio 90/10.

0.63 g of this mixture were treated with 30 mL of toluene and 1.2 g of PbCl$_2$ (4.31 mmol). The suspension obtained was stirred for 30 hours at room temperature and 12 hours at 40° C. $^1$H NMR analysis showed decomposition of the product to indene. The yield of the reaction to give Ind$_2$ZrClMe is 74%

COMPARATIVE EXAMPLE 12

0.67 g of CeCl$_3$ (Aldrich, MW=246.48, 2.72 mmol) were added to a suspension of Ind$_2$ZrMe$_2$ (experiment 20826/5, 0.91 g, MW=351.594, 2.59 mmol) in 30 mL of toluene, in a 100 mL Schlenk flask. The light brown suspension obtained was stirred 24 hours at room temperature, but no reaction was observed by $^1$H NMR analysis. It was then treated with additional 0.64 g of CeCl$_3$ (2.6 mmol) and stirred 3 hours at room temperature and 4 hours at 40° C. No reaction was observed by $^1$H NMR.

EXAMPLE 13

Synthesis of Ind$_2$ZrCl$_2$

A solution of SCl$_2$ (Riedel de Haen, 0.16 g, MW=102.966, 1.55 mmol) in 10 mL of CH$_2$Cl$_2$ was added to a brown suspension of Ind$_2$ZrMe$_2$ (experiment 20826/7-9, 0.55 g, MW=351.594, 1.56 mmol) in 10 mL of CH$_2$Cl$_2$. During the addition exothermicity was observed and the reaction mixture turned clearer. After 3 hours stirring at room temperature the reaction mixture turned reddish and $^1$H NMR analysis showed a mixture of Ind$_2$ZrCl$_2$ and Ind$_2$ZrMeCl in the ratio 61/39. Additional 0.055 g of SCl$_2$ (0.53 mmol) were added to the reaction mixture. After 1 hour stirring the brown suspension obtained was evaporated to dryness under reduced pressure to give 0.61 g (100% metal-based yield) of a clear brown powder, which $^1$H NMR analysis showed to be Ind$_2$ZrCl$_2$ with some impurities.

EXAMPLE 14

Synthesis of Ind$_2$ZrI$_2$

Crystals of I$_2$ (0.70 g, MW=253.809, 2.76 mmol) were added to a suspension of Ind$_2$ZrMe$_2$ (experiment 20826/7-9, 0.48 g, MW=351.594, 1.36 mmol) in 20 mL of CH$_2$Cl$_2$. The orange suspension turned to dark purple in few minutes. After 30 minutes stirring at room temperature, the suspension was evaporated to dryness under reduced pressure to give 0.83 g (100% yield) of an orange powder, which was characterized by $^1$H NMR as pure Ind$_2$ZrI$_2$.

$^1$H-NMR (CD$_2$Cl$_2$, δ, ppm): 6.42 (d, 4H, Cp-H(1,3), J=3.33 Hz); 6.64 (t, 2H, Cp-H(2), J=3.33 Hz); 7.30–7.40 (m, 4H, Ar); 7.66–7.75 (m, 4H, Ar).

EXAMPLE 15

Synthesis of Ind$_2$ZrBr$_2$

A solution of 0.52 g of Br$_2$ (Fluka, 3.69 mmol) in 7 ml of CH$_2$Cl$_2$ was added to a solution of 0.65 g of Ind$_2$ZrMe$_2$ (1.85 mmol) in 20 ml of CH$_2$Cl$_2$. The reaction was exothermic. The brown suspension obtained was stirred at room temperature for 18 hours and then evaporated to dryness under reduced pressure to give a reddish powder. This powder showed the presence of some impurity, so it was treated with ether and filtered. The residue was still not clean enough, so it was treated with toluene and filtered. The filtrate was evaporated to dryness under reduced pressure to give pure Ind$_2$ZrBr$_2$ which was characterized by $^1$H NMR.

$^1$H NMR (CD$_2$Cl$_2$, δ, ppm): 6.28 (d, 4H, Cp-H(1,3), J=3.42 Hz); 6.57 (t, 2H, Cp-H(2), J=3.42 Hz); 7.30–7.38 (m, 4H, Ar); 7.63–7.70 (m, 4H, Ar).

EXAMPLE 16

Synthesis of Me$_2$Si(Me$_4$Cp)(t-BuN)TiClMe 0.69 mL of SiCl$_4$ (5.98 mmoles) previously diluted in 2 mL of CH$_2$Cl$_2$ were added dropwise at romm temperature to a solution of 0.98 g of Me$_2$Si(Me$_4$ Cp)(t-BuN)TiMe$_2$ (obtained according to WO 00/75151) in 5 mL of CH$_2$Cl$_2$. After 6 h, the monochloro complex was obtained in nearly 100% yield.

EXAMPLE 17

Synthesis of (N-ethyl-5,6-dihydroindeno[2,1-b]indol-6-yl)(t-BuN)TiCl$_2$ 0.71 g of CuCl (6.85 mmoles) were added at room temperature to a solution of 0.6 g (1.37 mmoles) of dimethylsilyl(tert-butylamino)(N-ethyl-5,6-dihydroindeno[2,1-b]indol-6-yl)dimethyl titanium (obtained according to WO 01/53360) in 5 mL of CH$_2$Cl$_2$. The mixture of reaction was monitored by $^1$H-NMR after 1 h, 4 h and one night of stirring. The suspension was filtered and the filtrate was dried in vacuo obtaining a red-brown sticky solid (yield 100%). $^1$H-NMR shows the formation of dimethylsilyl(tert-butylamino)(N-ethyl-5,6-diydroindeno[2,1-b]indol-6-yl) dichloro titanium.

EXAMPLE 18

Synthesis of (N-ethyl-5,6-dihydroindeno[2,1-b]indol-6-yl)(t-BuN)TiCl$_2$ 0.7 mL (0.7 mmoles) of BCl$_3$ 1.0 M in heptane were added at 0° C. to a solution of 0.306 g (0.7 mmoles) of dimethylsilyl(tert-butylamino)(N-ethyl-5,6-dihydroindeno [2,1-b]indol-6-yl)dimethyl titanium (obtained according to WO 01/53360) in 8 mL of Et$_2$O, after 2 hours of stirring at room temperature the $^1$H-NMR analysis shows the formation of the dichloro complex. The solvent was dried in vacuo and the crude was washed with 7 mL of toluene, the residue was dried under reduced pressure, obtaining a red brown solid, which resulted almost pure desired product by $^1$H-NMR (yield 100%).

$^1$H-NMR (C$_6$D$_6$, δ, ppm): 0.61 (s, 3H, Si—CH$_3$); 0.75 (s, 3H, Si—CH$_3$); 1.15 (t, 3H, CH$_3$, J=7.24 Hz); 1.28 (s, 9H, t-Bu); 3.81 (q, 2H, CH$_2$, J=7.24 Hz); 6.98–7.92 (m, 8H, Ar).

$^1$H-NMR (CDCl$_3$, δ, ppm): 1.01 (s, 3H, Si—CH$_3$); 1.10 (s, 3H, Si—CH$_3$); 1.36 (s, 9H, t-Bu); 1.54 (t, 3H, CH$_3$, J=7.24 Hz); 4.38 (q, 2H, CH$_2$, J=7.24 Hz), 7.21–8.05 (m, 8H, Ar).

The invention claimed is:

1. A process for preparing dihalide or monohalide metallocene compounds of formula (I),

$$(Cp)(ZR^1{}_m)_n(A)_rML_qL'_s \qquad (I)$$

wherein $(ZR^1{}_m)_n$ is a divalent group bridging Cp and A; Z being C, Si, Ge, N or P, and the R$^1$ groups, equal to or different from each other, being hydrogen or linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl groups, optionally containing one or more heteroatoms belonging to groups 13–17 of the Periodic Table of the Elements or two R$^1$ can form a aliphatic or aromatic C$_4$–C$_7$ ring that can bear substituents;

Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms belonging to groups 13–17 of the Periodic Table of the Elements;

A is O, S, NR$^2$, PR$^2$, wherein R$^2$ is hydrogen, a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl, or a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms belonging to groups 13–17 of the Periodic Table of the Elements;

M is selected from zirconium, titanium or hafnium;

L, equal to or different from each other, are selected from the group consisting of chlorine, bromine, and iodine;

L' is selected from the group consisting of hydrogen, a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl group, optionally containing at least one Si or Ge atoms;

m is 1 when Z is N or P, and m is 2 when Z is C, Si or Ge;

n is 0, 1, 2, 3 or 4, being 0 when r is 0 or 2;

r is 0, 1 or 2;

q is 1, 2, or 3;

s is 0 or 1; wherein q+s=3−r;

said process comprising contacting a compound of formula (II)

wherein
y is equal to s+q;
with an halogenating agent selected from the group consisting of $T^1L_{w^1}$, $T^2L_{w^2}$, $O=T^3L_{w^3}$, and $R^6C(O)L$, mercury dichloride ($HgCl_2$) being excluded, wherein $T^1$ is a metal of groups 3–13 of the Periodic Table of Elements or of the lanthanides series;

$T^2$ is a nonmetal element of groups 13–16 of the Periodic Table of Elements with the exclusion of carbon;

$T^3$ is selected from the group consisting of C, P and S;

O is an oxygen atom bonded to $T^3$ through a double bond;

$R^6$ is selected from a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl;

H is hydrogen;

$w^1$ is equal to the oxidation state of the metal $T^1$;

$w^2$ is equal to the oxidation state of the element $T^2$;

$w^3$ is equal to the oxidation state of the element $T^3$ minus 2.

2. The process according to claim 1, wherein divalent bridge $(ZR^1_m)_n$ is selected from the group consisting of $CR^1_2$, $(CR^1_2)_2$, $(CR^1_2)_3$, $SiR^1_2$, $GeR^1_2$, $NR^1$ and $PR^1$;

Cp, which is π-bonded to said metal M, is selected from the group consisting of cyclopentadienyl, mono-, di-, tri- and tetra-methyl cyclopentadienyl; 4-tertbutyl-cyclopentadienyl; 4-adamantyl-cyclopentadienyl; indenyl; mono-, di-, tri- and tetra-methyl indenyl; 4,5,6,7-tetrahydroindenyl; fluorenyl; 5,10-dihydroindeno[1,2-b]indol-10-yl; N-methyl- or N-phenyl-5,10-dihydroindeno [1,2-b]indol-10-yl; 5,6-dihydroindeno[2,1-b]indol-6-yl; N-methyl- or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl and 2,5-dimethyl-cyclopenta[1,2-b:4,3-b']-dithiophene; and A is cyclopentadienyl, mono-, di-, tri- and tetra-methyl cyclopentadienyl; 4-tertbutyl-cyclopentadienyl; 4-adamantyl-cyclopentadienyl; indenyl; mono-, di-, tri- and tetra-methyl indenyl; 4,5,6,7-tetrahydroindenyl; fluorenyl; 5,10-dihydroindeno[1,2-b]indol-10-yl; N-methyl- or N-phenyl-5,10-dihydroindeno [1,2-b]indol-10-yl; 5,6-dihydroindeno[2,1-b]indol-6-yl; N-methyl- or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl; 2,5-dimethyl-cyclopenta[1,2-b:4,3-b']-dithiophene; N-methyl; N-ethyl; N-isopropyl; N-butyl; N-phenyl; N-benzyl; N-cyclohexyl; or N-cyclododecyl.

3. The process according to claim 2, wherein the divalent bridge $(ZR^1_m)_n$ is selected from the group consisting of $Si(CH_3)_2$, $SiPh_2$, $CH_2$, $(CH_2)_2$, $(CH_2)_3$ and $C(CH_3)_2$.

4. The process according to claim 1, wherein the halogenating agent is selected from the group consisting of $FeCl_3$, $CuCl_2$, $ZnCl_2$, $BCl_3$, $BBr_3$, $SiCl_4$, $PCl_5$, $SOCl_2$, $POCl_3$, $CH_3C(O)Cl$, $C_6H_5CH_2C(O)Cl$, $C_6H_5C(O)Cl$, $CH_3CH_2CH_2C(O)Cl$, $Br_2$, $Cl_2$, HBr and HI.

5. The process according to claim 1, wherein the process is carried out in an aprotic polar or apolar solvent.

* * * * *